United States Patent
Clossen-von Lanken Schulz et al.

(10) Patent No.: US 8,418,562 B2
(45) Date of Patent: Apr. 16, 2013

(54) DEVICE FOR NONDESTRUCTIVE MATERIAL TESTING OF A TEST SUBJECT USING ULTRASONIC WAVES

(75) Inventors: Michael Clossen-von Lanken Schulz, Issum (DE); Stefan Obermayr, Mülheim (DE); Michael Opheys, Nettetal (DE)

(73) Assignee: Siemens Aktiengesellschaft, München (DE)

( * ) Notice: Subject to any disclaimer, the term of this patent is extended or adjusted under 35 U.S.C. 154(b) by 322 days.

(21) Appl. No.: 12/919,040

(22) PCT Filed: Jan. 21, 2009

(86) PCT No.: PCT/EP2009/050614
§ 371 (c)(1),
(2), (4) Date: Aug. 24, 2010

(87) PCT Pub. No.: WO2009/106383
PCT Pub. Date: Sep. 3, 2009

(65) Prior Publication Data
US 2011/0000301 A1 Jan. 6, 2011

(30) Foreign Application Priority Data
Feb. 26, 2008 (EP) .................................. 08003487

(51) Int. Cl.
*G01N 29/04* (2006.01)
*G01D 21/00* (2006.01)
*B29C 35/08* (2006.01)

(52) U.S. Cl.
USPC .............................. 73/632; 73/866.5; 264/401

(58) Field of Classification Search .................... 73/632, 73/635, 636, 639, 866.5; 264/401
See application file for complete search history.

(56) References Cited

U.S. PATENT DOCUMENTS

| | | | |
|---|---|---|---|
| 4,235,112 A * | 11/1980 | Kaiser | 73/634 |
| 4,311,052 A | 1/1982 | Jeffras | |
| 4,621,430 A * | 11/1986 | Lenz | 33/711 |
| 4,742,713 A | 5/1988 | Abe | |
| 4,760,737 A | 8/1988 | Kupperman | |
| 5,339,692 A * | 8/1994 | Shoenhair et al. | 73/636 |
| 5,341,683 A * | 8/1994 | Searle | 73/597 |
| 5,386,727 A * | 2/1995 | Searle | 73/602 |
| 5,426,978 A * | 6/1995 | Imai | 73/622 |
| 5,710,378 A | 1/1998 | Dykes et al. | |
| 6,371,031 B1 * | 4/2002 | Muth | 105/96 |
| 6,661,126 B2 * | 12/2003 | Rudy | 310/12.09 |
| 6,722,202 B1 * | 4/2004 | Kennedy et al. | 73/634 |
| 7,194,908 B2 * | 3/2007 | Nenno et al. | 73/618 |

FOREIGN PATENT DOCUMENTS

| | | |
|---|---|---|
| CN | 2309562 Y | 3/1999 |
| CN | 1359659 A | 7/2002 |
| CN | 1447115 A | 10/2003 |

(Continued)

*Primary Examiner* — J M Saint Surin

(57) ABSTRACT

A device for the nondestructive material testing of an at least sectionally solid test subject by applying ultrasonic waves to the test subject and detecting the ultrasonic waves reflected inside the test subject is provided The device includes at least one testing head for transmitting the ultrasonic waves and for detecting the ultrasonic waves reflected from the test subject, at least one mobile carriage, on which the testing head is attached, and an elongate rail for guiding the carriage, which is adapted to the structure of the surface of the test subject. To this end, the carriage may be moved along the rail.

17 Claims, 4 Drawing Sheets

FOREIGN PATENT DOCUMENTS

| | | |
|---|---|---|
| CN | 1973776 A | 6/2007 |
| CN | 101002681 A | 7/2007 |
| CN | 200993651 Y | 12/2007 |
| EP | 0416245 A2 | 3/1991 |
| JP | 57113192 A | 7/1982 |
| JP | 61003059 A | 1/1986 |
| JP | 11304772 A | 11/1999 |
| JP | 2005504654 A | 2/2005 |

* cited by examiner

DEVICE FOR NONDESTRUCTIVE MATERIAL TESTING OF A TEST SUBJECT USING ULTRASONIC WAVES

CROSS REFERENCE TO RELATED APPLICATIONS

This application is the US National Stage of International Application No. PCT/EP2009/050614, filed Jan. 21, 2009 and claims the benefit thereof. The International Application claims the benefits of European Patent Office application No. 08003487.9 EP filed Feb. 26, 2002. All of the applications are incorporated by reference herein in their entirety.

FIELD OF INVENTION

The invention relates to a device for the nondestructive material testing of an at least sectionally solid test subject by applying ultrasonic waves to the test subject and detecting the ultrasonic waves reflected inside the test subject, according to the claims.

BACKGROUND OF INVENTION

In the case of many objects which are fully or partially formed solidly, their internal structure needs to be examined for material defects. To this end, nondestructive testing methods are required in order to obtain information about the internal structure which cannot be seen. This is necessary in particular for components subjected to heavy mechanical stress.

For example, steel components are forged after casting in order subsequently to be brought into their final shape by turning or other cold treatments. In this case, the testing for internal material defects may be carried out directly after forging.

Such components which are already in use must also be subjected regularly to material testing. This applies in particular to components which are exposed to heavy loads. The component to be tested may, for example, be a turbine blade for a gas or steam turbine. The turbine blade roots, in particular, are exposed to heavy loads during operation. These loads may lead to cracks, which can be detected and located with the ultrasonic measurement method by scanning the surface. Since the surface has a complex geometry, special measurement methods are necessary. Conventionally, such metal parts are tested using ultrasound. In this case, the sound waves which are reflected at interfaces inside the metal part are detected. With the time of flight of the reflected sound wave it is possible to detect, and from this the path length travelled and therefore the distance can be determined. By applying sound from different directions, further information can be obtained about the material defect or defects. From this, material defects can be located. For example, the geometrical orientation of the material defect can be determined in this way. From the shape of the reflected sound waves, deductions can be made about the type of material defect.

By scanning the surface of the test subject using an ultrasonic detector and recording the acquired data, the volume accessible to the ultrasound can be examined fully. From the acquired data, it is possible to generate an image which can be used for assessment.

In one known method, shaped parts are manufactured, for example from casting resin. These shaped parts can be applied with an accurate fit onto the surface to be scanned. The shaped parts contain holes into which an ultrasonic testing head is inserted. In order to be able to scan the entire surface to be tested, the ultrasonic testing head is displaced manually by discrete distances. This, however, is very laborious.

In another known method, the ultrasonic testing head is located on a carriage which is applied by means of a holding device on a neighboring test subject. The holding device can be moved by means of motors over the surface to be scanned. The testing head is pressed onto the surface of the test subject by springs. Optimal orientation of the testing head, however, is not possible in this case.

SUMMARY OF INVENTION

It is an object of the invention to provide a device for the nondestructive material testing of an at least sectionally solid test subject, of the type mentioned in the introduction, with which the possibilities for positioning the testing head are improved and the outlay on measurement technology is reduced.

This object is achieved by the subject-matter according to the claims.

According to the invention, the device mentioned in the introduction has the following components:
  at least one testing head for transmitting the ultrasonic waves and for detecting the ultrasonic waves reflected from the test subject,
  at least one mobile carriage, on which the testing head is attached or can be attached,
  an elongate rail for guiding the carriage, which is adapted or can be adapted to the structure of the surface of the test subject, wherein
  the carriage can be moved along the rail.

The testing head is arranged so that it can be moved relative to the carriage, which achieves at least one further degree of freedom for the movement of the testing head.

The essential point of the invention is that the carriage can be moved along a rail, and the rail can be applied onto the surface of the test subject. The rail in this case extends along a predetermined path on the surface of the test subject, and the carriage can be moved along this path. The carriage can be positioned at any desired location along the rail. The carriage can therefore be moved continuously along the rail.

Preferably, the rail is produced or can be produced by means of a stereolithography method. In this way, the rail can be produced, and adapted to the surface of the test subject, merely with the aid of a drawing of the surface of the test subject. The rail can therefore be adapted even to particularly complex surfaces.

According to the preferred embodiment, the rail is produced or can be produced from at least one material which can be cured by a treatment with ultraviolet light. The rail therefore initially consists of a flexible material and is correspondingly deformable. The rail can subsequently be cured in the desired shape. In this way, a matching rail and therefore a suitable testing device can be provided very rapidly for a particular test subject. For example, the rail is produced or can be produced from at least one epoxy resin.

In particular, the rail has one or more guiding grooves and/or guiding channels, which are formed complementarily to the carriage or are formed as a section of the carriage. This contributes to accurate guiding of the carriage in the rail.

Furthermore, the carriage may have at least one guiding roller. This allows low-friction, accurate movement of the carriage within the rail.

Preferably, at least one guiding roller and at least one guiding channel or guiding groove are engaged with one another or can be brought to engage with one another. The possibility for moving the carriage is therefore defined uniquely, i.e. along the rail.

According to the preferred embodiment, the carriage has at least one motor for driving the carriage along the rail. To this end, the carriage may have at least one gear wheel or the like coupled to the motor, which engages or can be brought to engage with the rail with a force fit. This creates a unique relationship between the number of full revolutions of the motor and the position of the carriage.

Furthermore, the rail may have at least one gear rack. As an alternative or in addition, at least one set of gear teeth may be formed in or on the rail. In this case, the gear wheel may engage or be brought to engage with the gear rack or the gear teeth. This leads to slip-free movement of the carriage.

Preferably, the testing head can be tilted on the carriage about an axis which extends parallel to the longitudinal axis of the rail. In this way, the detection region can be optimized with two degrees of freedom for the movement of the testing head.

Furthermore, the testing head and the carriage may be coupled to one another by at least one restoring apparatus. A stable position of the testing head can be defined and achieved in this way.

For example, the restoring apparatus has at least two magnet elements interacting with one another. As an alternative or in addition, the restoring apparatus may have at least one spring element.

Furthermore, at least two guiding rollers may be attached on the carriage in a mutually mobile fashion, so that the positions of the guiding rollers can be adapted to the profile of the rail. The effect which can be achieved by this is that the shape of the carriage is adapted to the rail in a simple way.

Preferably, the carriage comprises at least two frame parts which are connected or can be connected to one another in a tiltable fashion, at least one guiding roller being fastened rotatably on each part. In this case, the at least two frame parts may be tiltable about an axis which extends along the movement direction of the carriage. This allows particularly simple adaptation of the shape of the carriage to the profile of the rail.

For example, two guiding rollers are arranged next to one another on at least one frame part. In this case, this frame part with the two guiding rollers forms a rigid axle which can be tilted with respect to the upper frame part.

In the preferred embodiment, two guiding rollers are respectively arranged next to one another on at least two frame parts, so that the axles respectively having two guiding rollers can be tilted relative to one another.

For the coupling of the frame parts, the at least two frame parts may also be coupled to one another by at least one restoring apparatus.

For example, the restoring apparatus comprises at least two magnet elements interacting with one another. As an alternative or in addition, the restoring apparatus may have at least one spring element.

Furthermore, the device may have at least one control apparatus. The control apparatus may control both the transmission and the detection of the ultrasonic waves. Furthermore, the movement of the testing head and/or the carriage may also be controlled by the control apparatus.

In the preferred embodiment, the device is provided for the material testing of a test subject made of metal, and in particular for the material testing of a forged component. The device is particularly suitable for the material testing of a turbine wheel, a turbine wheel blade or a turbine wheel blade root. The dependent claims relate to other features, advantages and particular embodiments of the invention.

BRIEF DESCRIPTION OF THE DRAWINGS

The method according to the invention will be explained in more detail below in the description of the figures with the aid of preferred embodiments and with reference to the appended drawings, in which.

DETAILED DESCRIPTION OF INVENTION

Figure 1:
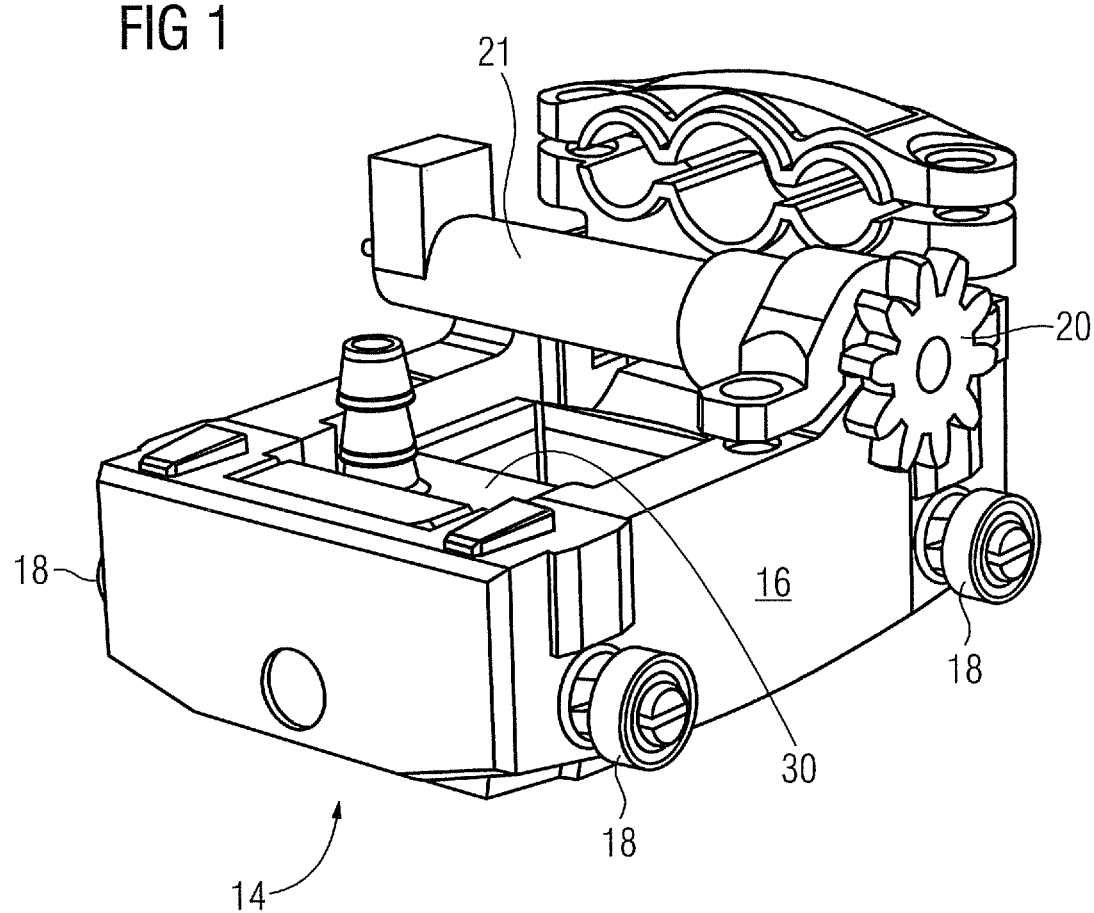
FIG. 1 shows a schematic perspective view of a carriage for a device for the nondestructive material testing of a test subject according to a preferred embodiment of the invention.

FIG. 1 shows a schematic perspective view of a carriage 14 for a device for the nondestructive material testing of a test subject according to a preferred embodiment of the invention.

The carriage 14 is formed essentially as a rectangular frame. The carriage 14 comprises a plurality of individual parts, most of which are made of plastic. On each of the two outer longitudinal sides 16 of the carriage 14, there are respectively two guiding rollers 18. The guiding rollers 18 are fastened on the carriage 14 so that they can rotate. In particular, the guiding rollers 18 are fastened on the rectangular frame so that they can rotate. In this specific embodiment, the guiding rollers 18 are made of metal. The rectangular frame is formed in two parts in this exemplary embodiment, as will be described in more detail below.

On one of the two longitudinal sides 16, there is a gear wheel 20 above the guiding rollers 18. The gear wheel 20 is likewise applied on this longitudinal side 16 so that it can rotate. The gear wheel 20 is furthermore configured as a drive wheel, and is driven by an electric motor 21.

The carriage 14 is intended to accommodate at least one testing head, which is not represented explicitly in FIG. 1. The carriage 14 essentially comprises the rectangular frame and a reception apparatus 30 for the testing head. The reception apparatus 30 for the testing head is applied by means of a restoring apparatus in the rectangular frame.

The testing head is intended to transmit the ultrasonic waves and to detect the ultrasonic waves reflected by the test subject. In the preferred embodiment, the testing head is applied on the carriage 14 so that it can be tilted. For example, the tilt axis extends parallel to the movement direction of the carriage 14.

In the preferred embodiment, the carriage 14 has a restoring apparatus, so that the testing head can be tilted automatically into a predetermined position, in particular into a central position. The restoring apparatus may have magnet elements or spring elements.

Figure 2:
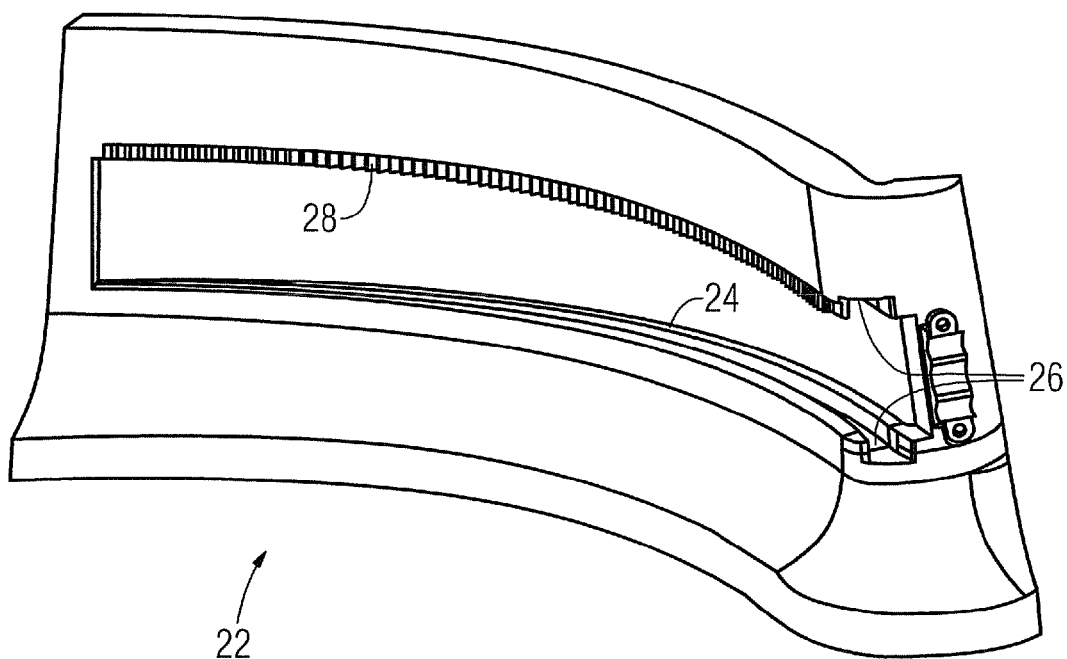
FIG. 2 shows a schematic perspective view of a rail for the device for the nondestructive material testing of the test subject according to the preferred embodiment of the invention.

FIG. 2 represents a schematic perspective view of a rail 22 for the device for the nondestructive material testing of the test subject according to the preferred embodiment of the invention.

In this preferred embodiment, the rail 22 is made of epoxy resin. The rail 22 can therefore be cured by a treatment with ultraviolet light. Furthermore, the rail 22 is preferably produced by means of a stereolithography method. This allows the rail to be produced merely with the aid of a drawing of the surface of the test subject.

The rail 22 is configured as an elongated rectangular frame. The contour of the rail 22 is adapted to the surface of the test body, so that one of the two large-area sides is formed essentially complementarily to the surface of the test subject and faces towards the test subject during the material testing.

On each of the two inner longitudinal sides 24, there is respectively a guiding channel 26. The two guiding channels 26 extend parallel to the longitudinal axis of the rail 22, with the two open sides of the guiding channels 26 facing towards one another. The guiding channels 26 are therefore open towards the inside. The rail 22 furthermore comprises a set of gear teeth 28, which extend in a similar way to a gear rack along the longitudinal axis of the rail 22.

The rail 22 and the carriage 14 are adapted to one another in respect of their geometry so that the carriage 14 can be displaced inside the rail 22. The guiding rollers 18 of the carriage 14 can in this case move in the guiding channels 26 of the rail 22, and the gear wheel 18 of the carriage 14 is engaged with the gear teeth 28.

Figure 3:
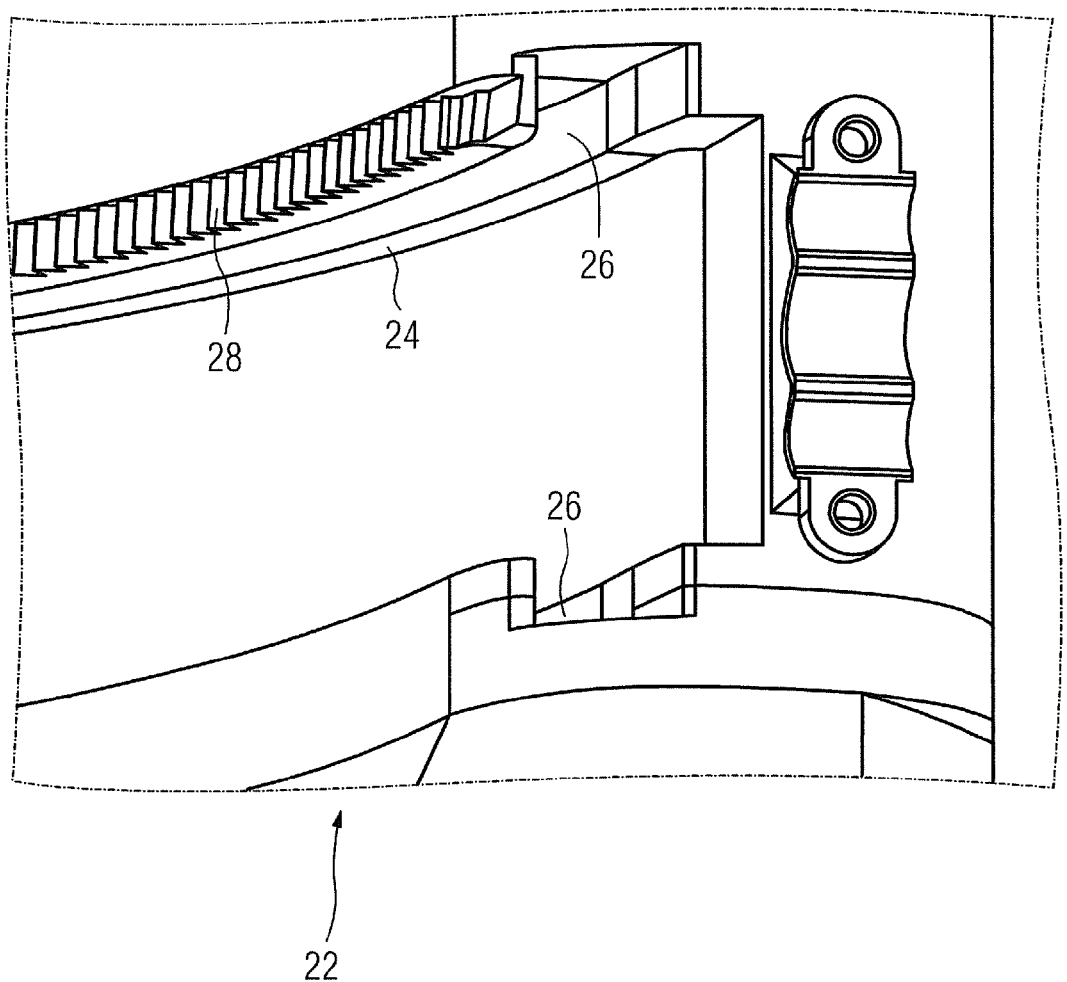
FIG. 3 shows a detailed perspective view of the rail for the device for the nondestructive material testing of the test subject according to the preferred embodiment of the invention.

FIG. 3 shows a detailed perspective view of the rail 22 for the device for the nondestructive material testing of the test subject according to the preferred embodiment of the invention. FIG. 3 illustrates some details of the rail 22. The guiding channels 26 are located on the two inner longitudinal sides 24. The two guiding channels 26 are also parallel to one another. The distance between the guiding channels 26 is essentially constant. The guiding channels 26 are open towards the inside, and their open sides faced towards one another. The set of gear teeth 28 is configured and arranged so that the gear wheel 20 engages with the gear teeth 28 and at the same time the guiding rollers 18 engage with the corresponding guiding channels 26.

Figure 4:
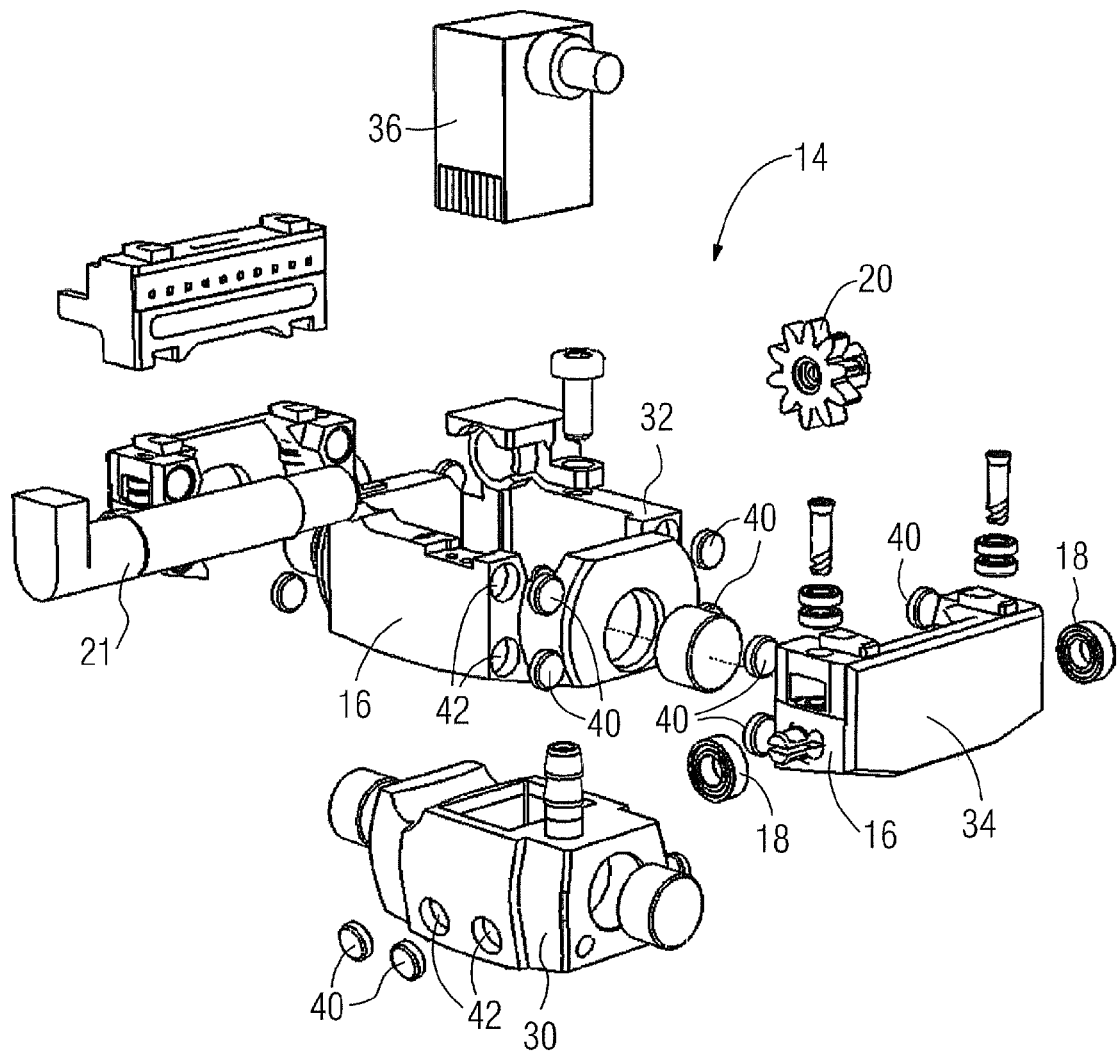
FIG. 4 shows a schematic perspective exploded view of the carriage with a testing head according to the preferred embodiment of the invention.

FIG. 4 shows a schematic perspective exploded view of the carriage 14 with a testing head 36 according to the preferred embodiment of the invention. The carriage 14 comprises the rectangular frame, which in turn has a first frame part 32 and a second frame part 34. The reception apparatus 30 for the testing head 36 is provided inside the first frame part 32. The testing head 36 is in turn provided inside the reception apparatus 30. The drive wheel, configured as a gear wheel 20, is driven by the electric motor 21.

Two guiding rollers 18, lying next to one another, are applied on the first frame part 32. Two further guiding rollers 18, lying next to one another, are applied on the second frame part 34. The first frame part 32 and the second frame part 34 are connected or can be connected to one another so that they can be tilted along the longitudinal axis of the carriage 14. The two axles of the guiding rollers 18 can therefore be tilted with respect to one another, so that the carriage 14 can be adapted to the profile of the rail 22. Owing to the tilting of the axles, all four guiding rollers 18 are always in contact with the rail 22.

The carriage 14 comprises a multiplicity of magnet elements 40, which form two restoring apparatuses. One restoring apparatus acts between the reception apparatus 30 and the first frame part 32. A further restoring apparatus acts between the first frame part 32 and the second frame part 34. On the reception apparatus 30, on the first frame part 32 and on the second frame part 34, there are holes 42 which are intended to accommodate the magnet elements 40. The holes 42 are slightly larger than the corresponding magnet elements 40.

The reception apparatus 30 can be tilted with respect to the first frame part 32 in two directions perpendicularly to the movement direction of the carriage 14, and can be restored automatically into a central position by means of the restoring apparatus. The second frame part 34 can likewise be tilted with respect to the first frame part 32, about the axis which extends parallel to the movement direction of the carriage 14, and restored automatically into a central position by means of the restoring apparatus. In the central positions, the corresponding openings face one another exactly.

The testing head can therefore on the one hand be moved along the rail 22 and on the other hand tilted perpendicularly to it, so that a comparatively large region can be exposed to sound and detected. Only two degrees of freedom of movement are required for the testing head, so that a relatively simple algorithm is sufficient for controlling the testing head and detecting and evaluating the reflected sound waves.

The material testing is carried out by moving a testing head, which is applied on the carriage 14, along the rail 22 and therefore along the outer surface of the test subject. The testing head can be tilted about an axis which is parallel to the longitudinal axis, and at least to the tangent of the rail 22.

With the device according to the invention, it is not absolutely necessary to scan the entire surface of the test subject in order to acquire the full volume of the test subject. A particular section or a particular path on the surface may for example be scanned, since owing to the tilting movements of the testing head at least the relevant region of the volume can be acquired even without full scanning of the surface.

The invention claimed is:

1. A device for the nondestructive material testing of an at least sectionally solid test subject by applying ultrasonic waves to the test subject and detecting the ultrasonic waves reflected inside the test subject, comprising:
    a testing head transmitting the ultrasonic waves and detecting the ultrasonic waves reflected from the test subject;
    a reception apparatus accommodating the testing head;
    a mobile carriage, on which the testing head is attached or attached; and
    a portable elongate rail guiding the carriage, which is applied onto a surface of the test subject whereby extending along a predetermined path on the surface of the test subject,
    wherein the mobile carriage moves along the elongate rail,
    wherein the testing head moves relative to the mobile carriage,
    wherein the testing head and the mobile carriage are coupled to one another by a restoring apparatus so that the reception apparatus is restored automatically into a central position using the restoring apparatus,
    wherein the elongate rail is produced using a stereolithography method or from a material which is cured by a treatment with ultraviolet light, and
    wherein the elongate rail includes a guiding groove and/or a guiding channel, which is formed complementarily to the mobile carriage or is formed as a section of the mobile carriage.

2. The device as claimed in claim 1, wherein the elongate rail is produced from an epoxy resin.

3. The device as claimed in claim 1, wherein the mobile carriage includes a guiding roller.

4. The device as claimed in claim 3, wherein the guiding roller and the guiding channel are engaged with one another.

5. The device as claimed in claim 1, wherein the mobile carriage includes a motor for driving the mobile carriage along the elongate rail.

6. The device as claimed in claim 5, wherein the mobile carriage includes a gear wheel coupled to the motor, which engages with the elongate rail by a force fit.

7. The device as claimed in claim 6, wherein the elongate rail includes a gear rack.

8. The device as claimed in claim 7, wherein a set of gear teeth is formed in or on the elongate rail.

9. The device as claimed in claim 8, wherein the gear wheel engages with the gear rack or the gear teeth.

10. The device as claimed in claim 1, wherein the testing head may be tilted on the mobile carriage about an axis which extends parallel to a longitudinal axis of the elongate rail.

11. The device as claimed in claim 1, wherein the restoring apparatus includes at least two magnet elements interacting with one another.

12. The device as claimed in claim 1, wherein the restoring apparatus includes a spring element.

13. The device as claimed in claim 1, wherein at least two guiding rollers are attached on the mobile carriage in a mutually mobile fashion, so that the positions of the at least two guiding rollers may be adapted to a profile of the elongate rail.

14. The device as claimed in claim 1, wherein the mobile carriage comprises at least two frame parts which are connected in a tiltable fashion, at least one guiding roller is fastened rotatably on each part.

15. The device as claimed in claim 14, wherein the at least two frame parts may be tilted about an axis which extends along a movement direction of the mobile carriage.

16. The device as claimed in claim 14, wherein two guiding rollers are arranged next to one another on at least one frame part.

17. The device as claimed in claim 16, wherein two guiding rollers are respectively arranged next to one another on at least two frame parts, so that two axles respectively including two guiding rollers may be tilted relative to one another.

* * * * *